United States Patent [19]

Ichikawa et al.

[11] Patent Number: 4,893,510
[45] Date of Patent: Jan. 16, 1990

[54] METHOD OF MEASURING DISTRIBUTION OF CRYSTAL GRAINS IN METAL SHEET AND APPARATUS THEREFOR

[75] Inventors: Fumihiko Ichikawa, Yotsukaido; Hajime Takada; Kazuya Asano, both of Chiba, all of Japan

[73] Assignee: Kawasaki Steel Corporation, Hyogo, Japan

[21] Appl. No.: 270,648

[22] Filed: Nov. 14, 1988

[30] Foreign Application Priority Data

Nov. 16, 1987 [JP] Japan .................................. 62-289019
Sep. 20, 1988 [JP] Japan .................................. 63-235294

[51] Int. Cl.$^4$ ............................................. G01N 29/00
[52] U.S. Cl. ......................................... 73/620; 73/630; 73/599
[58] Field of Search ................. 73/620, 630, 599, 159, 73/615, 618, 588, 600

[56] References Cited

U.S. PATENT DOCUMENTS

3,929,006 12/1975 Boggs et al. ........................... 73/615
4,563,898 1/1986 Kanda et al. ........................... 73/606

*Primary Examiner*—John Chapman
*Assistant Examiner*—Michele Simons
*Attorney, Agent, or Firm*—Oliff & Berridge

[57] ABSTRACT

In measuring a distribution of crystal grains in metal sheet, an exciting frequency of ultrasonic wave is determined such that a wavelength of the ultrasonic wave propagated in a direction of the sheet thickness of the grains each having an aimed orientation is set at a value of twice the thickness of the sheet multiplied by about integers or about half integers, burst-like ultrasonic pulses having this frequency and including two or more waves are directed into the direction of the sheet thickness by use of an ultrasonic probe moving relatively with a body to be measured, multiple reflected waves generated from the bottom and top faces of the metal sheet upon the reflection from the sheet surface are caused to interfere with each other, the multiple reflected waves, which have interfered with each other, are detected, orientation of the grains in the metal sheet are estimated from the magnitudes in amplitude of the interferent multiple reflected waves thus detected, and the distribution of the grains in orientation in various portions, into which the ultrasonic wave is directed, is detected two-dimensionally.

10 Claims, 9 Drawing Sheets

$V_1 (\times 10^3 m/sec)$

METHOD OF MEASURING DISTRIBUTION OF CRYSTAL GRAINS IN METAL SHEET AND APPARATUS THEREFOR

BACKGROUND OF THE INVENTION (1) Field of the Invention

The present invention relates to a method of measuring a distribution of crystal grains in metal sheet and an apparatus therefor. More particularly, the present invention relates to a highly practical method of measuring a distribution of crystal grains in metal sheet and an apparatus therefor, suitable for use in producing an anisotropic silicon steel sheet high in electromagnetic properties in a rolling direction, capable of non-destructively measuring the distribution of crystal grains in orientation of the anisotropic silicon steel sheet on line.

(2) Prior Art

For the purpose of applying it to a core of an AC step-up transformer and the like, there has been produced an anisotropic silicon steel sheet high in electromagnetic properties in the rolling direction. This anisotropic silicon steel sheet is produced by obtaining the crystal grains directed in a so-called GOS orientation, in which a plane {110} is parallel to the sheet surface and a direction <100> is parallel to the rolling direction.

The larger the number of the grains close to the GOS orientation is, the higher the electromagnetic properties of the anisotropic silicon steel sheet are. However, in the actual manufacturing process, it is not necessarily possible to produce only the grains close to the GOS orientation. Due to a change in the conditions of manufacture or a disturbance, grains greatly shifted from this GOS orientation, i.e. so-called abnormal grains are formed.

Figure 14:
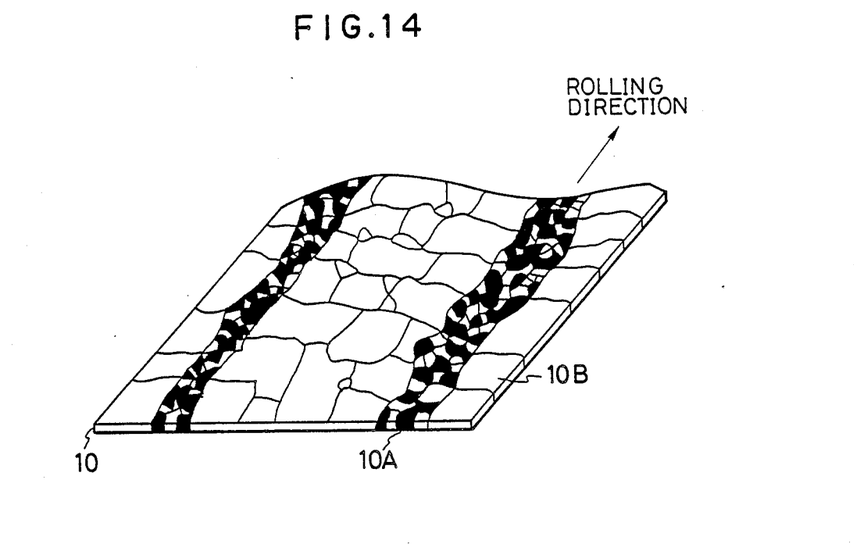
FIG. 14 is a perspective view showing the silicon steel sheet containing therein the abnormal grains in a typified manner.

FIG. 14 shows a typified view of a product 10 including the abnormal grains 10A. A normal grain 10B close to the GOS orientation has a grain diameter as large as several mm-several cm, however, the abnormal grain 10A has a grain diameter of several mm or less in general, the orientation of the grain is directed in random directions, and is distributed such that it extends generally in the rolling direction as shown in FIG. 14.

In the manufacturing process of the above-described anisotropic silicon steel sheet, as instruments for detecting the electromagnetic properties of the product, an Epstein detector and a single sheet tester are used off line, while a continuous iron loss tester is used on line, thus measuring an iron loss of the steel sheet and a density of magnetic fluxes. However, the aforesaid measuring instruments can measure only the mean electromagnetic properties in the widthwise direction of the steel sheet, but cannot measure the distribution of the abnormal grains 10A.

On the other hand, as a method of measuring the distribution of the abnormal grains of the silicon steel sheet, there is a macro-etch method, wherein the product is cut into strip-like forms, an insulation coating film on the surface thereof is peeled off and the surface is etched by use of a Nital etchant, whereby the fact that etched effects are different in accordance with the orientations of the crystal grains is utilized, so that the distribution of the crystal grains is observed.

However, application of this macro-etch method is limited to off line, but cannot be applied to on line. Moreover, it is necessary to cut the product into the strip-like forms. Further, etching can be made only after the insulation coating film is peeled off. Thus, much labor is needed, and there is the problem of handling such as a treatment of chemicals. In addition, since this is a destructive test and a sampling inspection, the quality of the product over the total length thereof cannot be ensured. Further, such a problem is presented that the efficiency is low and so forth from the viewpoint of the type of working.

On the other hand, as techniques relating to the present invention, there has been proposed a method of non-destructively testing the characteristic of a steel sheet by the utilization of propagation characteristics of ultrasonic wave in the crystal.

More specifically, in general, a sonic speed v of a longitudinal ultrasonic wave propagated in a direction of $<n_1, n_2, n_3>$ of a body of isometric crystal is given as a root of the following equation.

$$(\rho v^2 - C_{44})^3 - a(\rho v^2 - C_{44})^2 + c(a+b)(n_1^2 n_2^2 + n_2^2 n_3^2 + \quad (1)$$
$$n_3^2 n_1^2)(\rho v^2 - C_{44}) - c^2(a+2b) n_1^2 n_2^2 n_3^2 = 0$$

where $n_1$, $n_2$, and $n_3$ are direction cosines between the propagated direction and the principal axis of crystal, and a, b and c are shown in the following equations, respectively.

$$a = C_{11} - C_{44} \quad (2)$$

$$b = C_{12} + C_{44} \quad (3)$$

$$c = C_{11} - C_{12} - 2C_{44} \quad (4)$$

where Cij is an ij component of an elastic matrix.

Accordingly, when the body is steel, and an elastic constant of steel is given, whereby a sonic speed v of the longitudinal ultrasonic wave propagated in a single crystal in various directions can be calculated from the equation (1).

Figure 15:
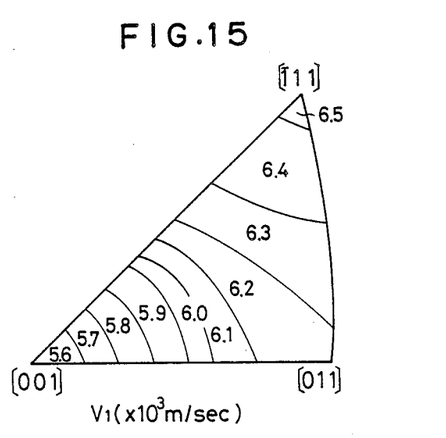
FIG. 15 is a stereo-projection view showing the changes in the sonic speed according to the orientations in the single crystal in the silicon steel.

FIG. 15 shows examples of calculated results in forms on a stereo-projection drawing. Because the sonic speed v is different in accordance with the propagated directions of the ultrasonic wave, the sonic speed v is measured, so that the orientation of the crystals can be determined to a certain extent. For example, when the direction of the sheet thickness is given as the Z-axis, a sonic speed v in the direction of the Z-axis is measured and, when the measured value is 6500 m/s, it can be said that, in this body, an axis [111] of the crystal is laid in the direction of the sheet thickness.

As the conventional example of the measurement of the characteristics of a material by the utilization of the characteristics of the ultrasonic wave propagated in a crystal as described above, there is a method of discriminating a cast structure by the ultrasonic wave as disclosed in Japanese Patent Unexamined, Publication No. 126992/1978. According to this method, a propagation time of the ultrasonic wave in the direction of the sheet thickness of a poly-crystalline body is measured, and from this measured value, a thickness of a columnar crystal and a thickness of an isometric crystal are estimated.

Figure 16:
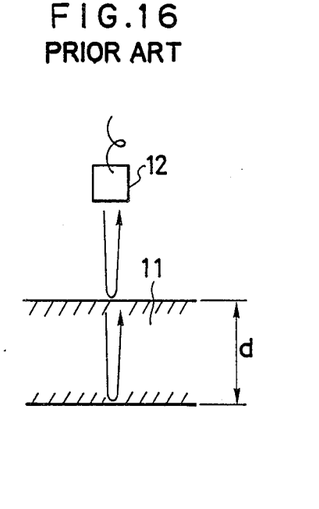
FIG. 16 is a sectional view showing the conventional sonic speed measurement utilizing the multiple reflections, in a typified manner.
Figure 17:
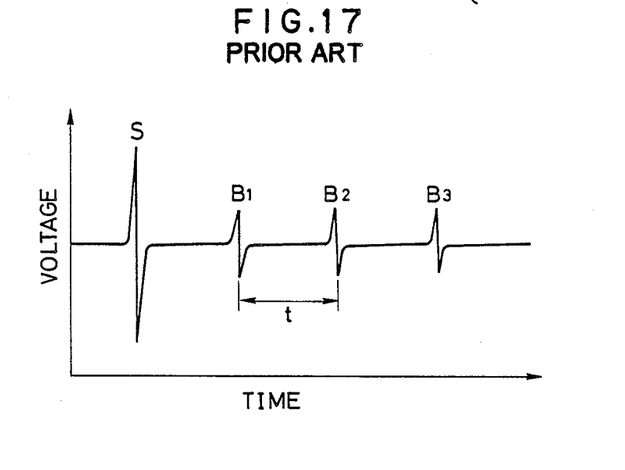
FIG. 17 is a chart showing examples of the measured wave forms by the sonic speed measurement utilizing the multiple reflections.

When a sonic speed in the direction of sheet thickness of a body is to be measured in general, as shown in FIG. 16, ultrasonic wave is directed toward a body 11 to be measured in the direction of sheet thickness by use of an ultrasonic probe 12, a time interval t of a row of bottom echoes B1, B2 and B3 which are produced thereby as shown in FIG. 17, for example, is measured, and the sonic speed v is calculated by the following equation.

$$v = 2d/t \qquad (5)$$

where d indicates a sheet thickness of the body 11. In addition, S denotes a signal produced by a surface reflected wave.

However, also in this method, when the sheet thickness reaches a length close to a wavelength of the ultrasonic wave, B1, B2 and B3 in the row of bottom echoes overlie one another, the time interval t cannot be measured.

For example, if a frequency of the ultrasonic wave is 10 MHz, the wavelength of the longitudinal wave is about 0.6 mm, while the sheet thickness d of the silicon steel sheet 11 to be measured is 0.1–0.5 mm, then this method is not applicable.

In order to apply this method, it is necessary that the frequency of the ultrasonic wave be 100 MHz or thereabove and short pulses are adopted, whereby the problems of electric circuits, largely attenuated ultrasonic wave and the like are raised, so that this method becomes unpractical.

Figure 18:
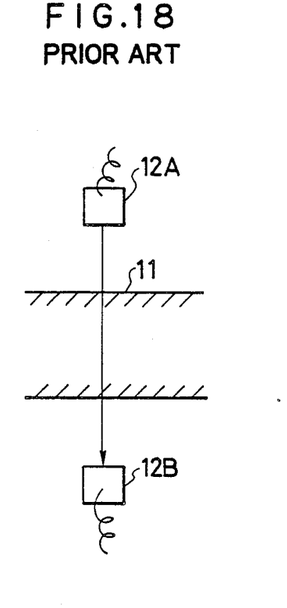
FIG. 18 is a sectional view showing the conventional sonic speed measurement utilizing the transmission method, in a typified manner.

On the other hand, in FIG. 18 for example, a method not utilizing the row of bottom echoes is shown. In this method, the body 11 to be measured is interposed between a transmitting element 12A and a receiving element 12B of ultrasonic wave, whereby a penetration time difference ti of the ultrasonic wave is measured. In this case, the relationship between the penetration time difference ti and the sonic speed v is shown by the following equations.

$$ti = d/v + (l_1 + l_2)/V_0 \qquad (6)$$

$$\Delta ti = d\Delta v/v^2 \qquad (7)$$

Accordingly, when the sonic speed v is to be determined at an accuracy of 1% for example, the sonic speed v = 6000 m/s, sheet thickness d = 0.3 mm and $\Delta v/v = 0.01$ are substituted into the equation (7) to obtain $\Delta ti = 5 \times 10^{-10}$ sec. At this time, it is necessary to keep constant a distance between ultrasonic probes 12A and 12B with a permissible fluctuation only 0.75 micrometer. This value is achievable in a research laboratory, however, it is very impractical.

SUMMARY OF THE INVENTION

The present invention has been developed to obviate the above-described disadvantages of the prior art and, it is an object of the present invention to provide a practical method of measuring a distribution of crystal grains in metal sheet and an apparatus therefor, in which it is possible to efficiently detect the distribution of the abnormal grains of the metal sheet non-destructively and on line and to ensure the quality over the total length thereof without the need of cutting the product into strip-like forms and peeling off the insulation coating film as in the macro-etch method.

To achieve the above-described object, the present invention comprises a method for measuring the distribution of the crystal grains in metal sheet, comprising:

determining an exciting frequency of ultrasonic wave such that a wavelength of the ultrasonic wave propagated in a direction of the sheet thickness of the grains each having an aimed orientation is set at a value of twice the thickness of the sheet multiplied by about integers times or about half integers;

directed into the sheet thickness ultrasonic pulses having this frequency and including two or more waves by use of at least one ultrasonic probe moving relatively with a body to be measured;

causing multiple reflected waves generated from the bottom and top faces of the metal sheet upon the reflection from the sheet surface to interfere with each other;

detecting the multiple reflected waves, which have interfered with each other;

estimating orientations of the grains in the metal sheet from the magnitudes in amplitude of the interferent multiple reflected waves; and the distribution of two-dimensionally detecting the grains in orientation in various portions, into which the ultrasonic wave is directed.

Furthermore, the exciting frequency of the ultrasonic wave is determined such that the wavelength of the ultrasonic wave is set at a value slightly shifted from value of the twice the thickness of the sheet multiplied by about integers or about half integers.

According to the present invention, an apparatus for measuring the distribution of crystal grains in metal sheet comprises:

ultrasonic probes, one acting as a transmitting element and the other as a receiving element, which are respectively provided at positions opposed to each other and on opposite sides of a body to be measured, for interchanging an electric signal and ultrasonic wave;

a transmitting means for delivering to the transmitting element two or more continuous burst wave electric signals having a frequency determined such that a wavelength of the ultrasonic wave propagated in a direction of the sheet thickness of the crystal grains each having an aimed orientation is set at a value of twice the thickness of the sheet multiplied by about integers or about half integers;

a receiving means for receiving a signal generated at the receiving element;

a means for taking out a signal produced by the interference between multiple reflected waves from the bottom and top faces of the metal sheet, which are generated upon the reflection from the sheet surface, from signals received by the receiving means; and a means for determining whether the orientation of the grains at portions, into which the ultrasonic wave is directed, is normal or not, from the magnitudes in amplitude of the interferent multiple reflected waves.

Furthermore, the ultrasonic probe is formed into a focus type ultrasonic probe capable of converging the ultrasonic wave, and the focal position thereof is made substantially coincident with the center of the sheet thickness of the body to be measured.

Furthermore, according to the present invention, the apparatus for measuring the distribution of the crystal grains in metal sheet comprises:

an ultrasonic probe acting as a transmitting element and a receiving element, which is provided on one side of a body to be measured, for interchanging an electric signal and ultrasonic wave;

a reflecting plate provided on the other side of the ultrasonic probe such that the body is between the reflecting plate and the ultrasonic probe;

a transmitting means for transmitting two or more continuous burst wave electric signals having a frequency determined such that a wavelength of the ultrasonic wave propagated in a direction of the sheet thickness of the crystal grains each having an aimed orientation is set at a value of twice the thickness of the sheet multiplied by about integers or about half integers, to the ultrasonic probe;

a receiving means for receiving a signal generated at the ultrasonic probe after being reflected by the reflecting plate and penetrating through the body again;

a means for taking out a signal produced by the interference between multiple reflected waves from the bottom and top faces of the metal sheet, which are generated upon the reflection from the sheet surface, from signals received by the receiving means; and a means for determining whether the orientation of the grains at portions, into which the ultrasonic wave is directed, is normal or not, from the magnitudes in amplitude of the interferent multiple reflected waves.

In addition, an ultrasonic wave reflecting portion of the reflecting plate is made to be concave, and the ultrasonic wave reflected by this concave surface is focused at about the center of the sheet thickness of the body again.

Furthermore, according to the present invention, the apparatus for measuring the distribution of the crystal grains in metal sheet comprises:

a least one ultrasonic probe for interchanging an electric signal and ultrasonic wave;

a scanner for scanning the ultrasonic probe or probes in the two dimensional directions;

a pulser for transmitting two or more continuous burst wave electric signals having a frequency determined such that a wavelength of the ultrasonic wave propagated in a direction of the sheet thickness of the crystal grains each having an aimed orientation is set at a value of twice the thickness of the sheet multiplied by about integers or about half integers;

a receiver for receiving a signal from the ultrasonic probe;

a timing control circuit for controlling the driving of the pulser;

a gate circuit for taking out only a signal produced by the interference between multiple reflected waves from the bottom and top faces of the metal sheet, excluding signals generated by the reflected waves from the sheet surface, in synchronism with a pulse emitted form the timing control circuit;

a peak hold circuit for holding a peak value of the interferent signal for a predetermined period of time;

an analog/digital converter for analog/digital converting an output from the peak hold circuit;

a processing unit for receiving an output from the analog/digital converter and performing a predetermined operation to determine whether the orientation of the crystal grains at portions, into which the ultrasonic wave is directed, is normal or not, and calculating the distribution of the grains having abnormal orientations on the basis of positional information from the scanner; and a display unit for displaying the calculated results.

Figure 2:
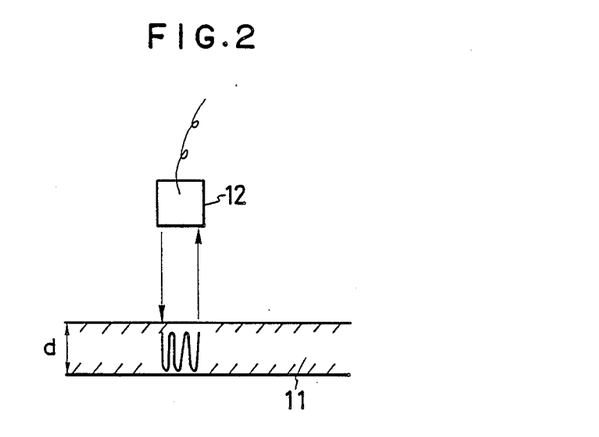
FIG. 2 is a typified view of the sonic speed measurement utilizing the interferent multiple reflections, for explaining the principle of the present invention.

To obviate the disadvantages of the conventional ultrasonic wave method, the inventors of the present invention have found that, without directly detecting the sonic speed of the ultrasonic wave, a change in the sonic speed can be converted into the intensity of the interference by utilizing the interference of the ultrasonic wave and detecting the intensity so that information corresponding to the sonic speed can be obtained. More specifically, as shown in FIG. 2, when ultrasonic pulses vertically fall into the body 11 to be measured (metal sheet) having a sheet thickness d from the probe 12 through a contacting medium (water for example), the reflection and penetration of the ultrasonic wave occur on the upper and under surfaces of the sheet, whereby multiple reflected waves are observed.

Figure 3:
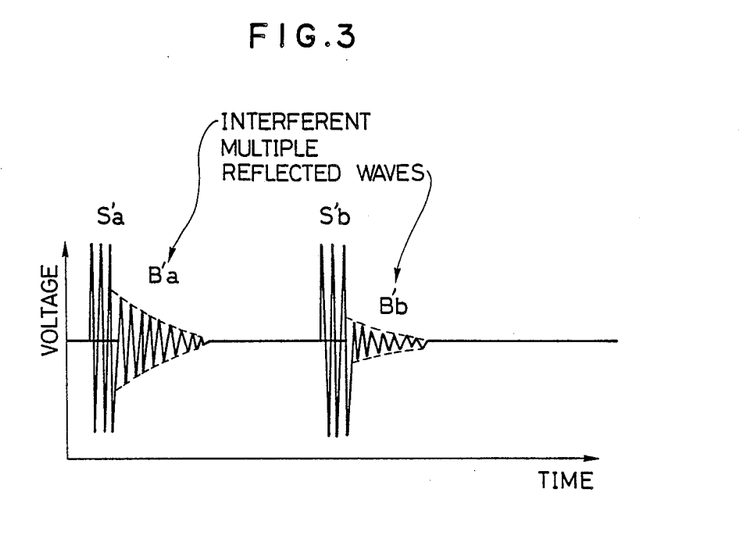
FIG. 3 is a chart showing an example of the measured wave forms by the interferent multiple reflection.

When the wavelength of the ultrasonic wave and the sheet thickness d are about equal in magnitude to each other, the multiple reflected waves overlie each other, whereby the interference occurs as shown in FIG. 3. In this interference, when the multiple reflected waves do not agree with each other at the phase of 180°, the multiple reflected waves offset each other (interferent multiple reflected wave signal Bb'). On the other hand, when the multiple reflected waves agree with each other at the phase of 0°, the multiple reflected waves intensify each other (interferent multiple reflected wave signal Ba'). In FIG. 3, Sa' and Sb' each denote a surface reflected wave signal.

The condition of interference is established when an exciting frequency f of the ultrasonic wave satisfies the following equation.

$$f = v/2d \qquad (8)$$

In order for the ultrasonic wave to interfere, it is necessary that the ultrasonic wave is a wave including at least two pulses or more, that is, a burst wave.

Figure 4:
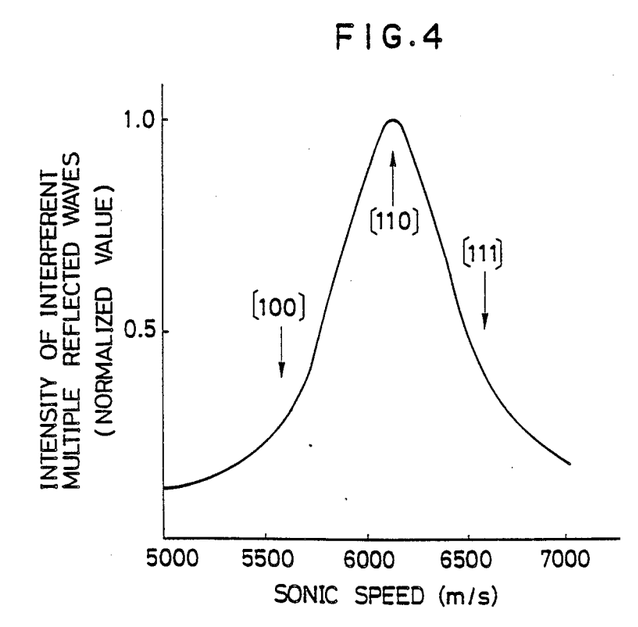
FIG. 4 is a chart showing an example of the relationship between the intensity of the interferent multiple reflected waves and the sonic speed, for explaining the principle of the present invention.

The normal grains in a silicon steel sheet takes the GOS orientation. At this time, the axis of crystal in the direction of the sheet thickness is <110> and the sonic speed in this direction is 6200 m/s. Then, when the sheet thickness d is set at 0.3 mm, the exciting frequency of the ultrasonic wave f at 10.33 MHz and the number of the burst waves at 10, if the relationship between the sonic speed v and the intensity of the interferent multiple reflected waves is calculated, then the results as shown in FIG. 4 are obtained.

The normal grains in the anisotropic silicon steel sheet take the GOS orientation, and shifts in orientation are within 10° at the most. When this is converted into a sonic speed in the direction of the sheet thickness, the distribution of 6200±50 m/s is obtained. Accordingly, the intensity of the interferent multiple reflected waves is monitored, and, when it becomes lower than a certain value, it is possible to determine the presence of the abnormal grains. In actuality, as shown in FIG. 14, the abnormal grains 10A have very small grain diameters as compared with those of the normal grains 10B and the distribution thereof is concentrated, and the orientations of the respective grains are random. Accordingly, even if a threshold value for detecting only the grains having orientations <111> and <100> is adopted, the distribution of the abnormal grains can be detected.

A first point to be noted in working the present invention is that, as shown in FIG. 3, the interferent multiple reflected waves Ba' and Bb' occur upon the occurrence of the surface reflected waves Sa' and Sb' which are first reflected waves of the incident wave in the boundary between the surfaces of a contact medium (water) and the body to be measured (metal sheet) and have high amplitudes, so that the surface reflected waves should not be detected.

There are methods described hereunder as the method of facilitating the detection of only the interferent multiple reflected waves without detecting the upper surface reflected waves of the body to be measured.

Figure 5:
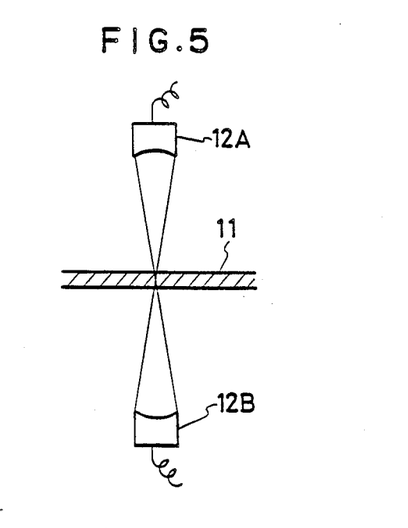
FIG. 5 is a sectional view showing the essential portion of an example of the method of the present invention utilizing the transmission method.

(a) As shown in FIG. 5, a transmitting element 12A and a receiving element 12B of ultrasonic wave, which are on opposite sides of the body 11 to be measured, are provided for detecting the penetrating ultrasonic wave (Transmission method).

Figure 6:
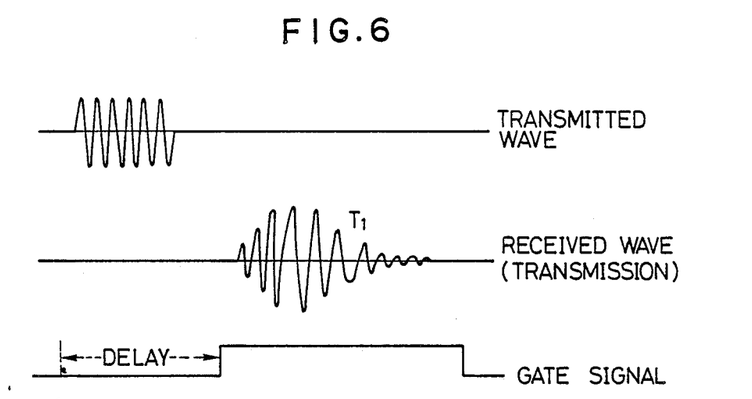
FIG. 6 is a chart showing an example of the received wave forms obtainable by the method of the present invention as shown in FIG. 5.

With this arrangement, the surface reflected waves reflected at the upper surface of the body 11 and having high intensity do not reach the receiving element 12B. Accordingly, a received signal is limited to only an interferent multiple wave signal T1, and the peak thereof is easily detected, as shown in FIG. 6.

As shown in FIG. 5, a focus type ultrasonic probe capable of converging the ultrasonic wave is used as the ultrasonic probe 12, and the focal position thereof is made substantially coincident with the center of the sheet thickness of the body 11, so that a spatial resolution in measuring can be improved.

Figure 7:
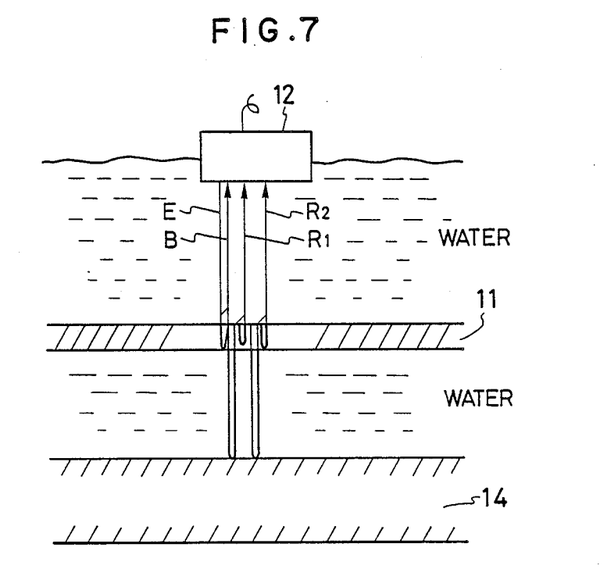
FIG. 7 is a sectional view showing the essential portion of another example of the method of the present invention utilizing the reflecting plate method.

(b) As shown in FIG. 7, the ultrasonic probe 12, which acts as the transmitting and as the receiving element is provided on one side and a reflecting plate 14 having a thickness not allowing the multiple reflected waves to interfere therewith is provided on the other side, such the body 11 to be measured is positioned therebetween, whereby the ultrasonic wave is reflected by the reflecting plate 14, so that the magnitude of a signal obtained by the ultrasonic wave having penetrated through the body 11 again can be detected (Reflecting plate method).

Figure 8:
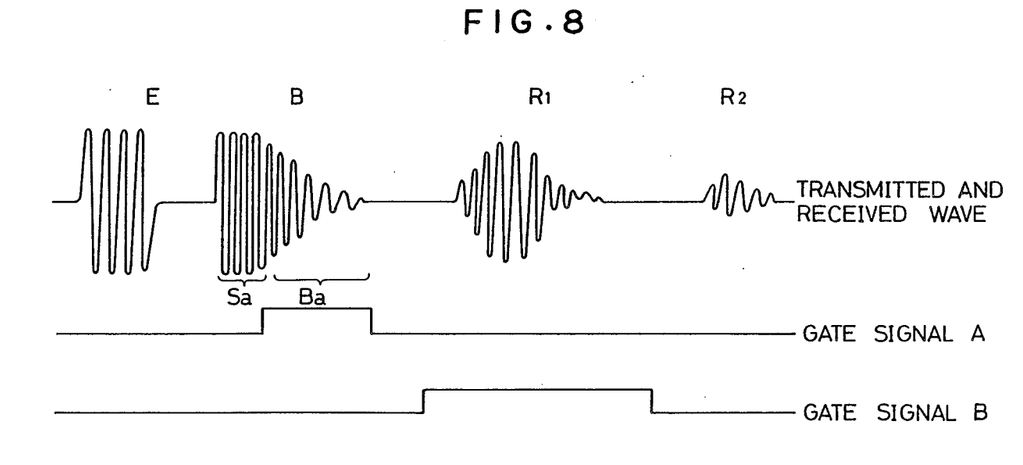
FIG. 8 is a chart showing an example of the received wave forms obtainable by the method of the present invention as shown in FIG. 7.

In this case, signals received by the ultrasonic probe 12 are shown in FIG. 8, and, out of these signals, R1 is a signal to be detected, and the surface reflected wave B reflected by the upper surface of the body 11 and having the high intensity is not included. Accordingly, by a gate signal B shown in the bottom stage in FIG. 8, it becomes easy to detect a peak of the aimed interferent multiple wave signal R1. In FIG. 8, Sa indicates a signal reflected by the surface of the body 11, and Ba denotes interferent multiple echoes occurring upon the occurrence of Sa. This Ba can be taken out by a gate signal A shown in the middle stage in FIG. 8.

Figure 9:
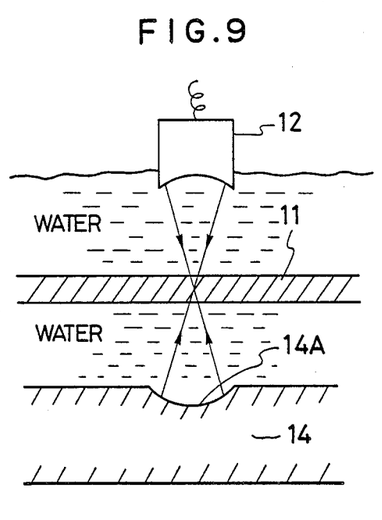
FIG. 9 is a sectional view showing the essential portion of an improved example of the method of the present invention utilizing the reflecting plate method.

According to this reflecting plate method, as shown in FIG. 9, a portion on the reflecting plate 14, to which the ultrasonic wave is applied, is formed into a concave surface 14A, whereby the ultrasonic wave is focused at about the center of the sheet thickness of the body 11 again, so that the spatial resolution in measuring can be improved.

According to the above-described two methods (a) and (b), not only the interferent multiple reflected waves are easily detected, but also, when the present invention is applied to an on-line measurement, even if the body 11 flucuates vertically, the influence thereof can be advantageously minimized. In addition, when the influence of the surface reflected waves reflected by the upper surface of the body 11 and having high intensity are not a problem, or, when the influence can be removed by other means such as a gate circuit and the like, the simple arrangement of a reflection method as shown in FIG. 2 can be adopted.

Figure 10:
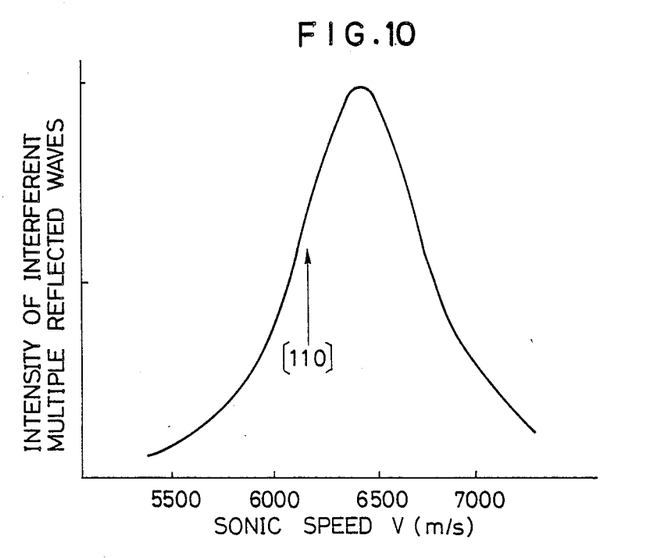
FIG. 10 is a chart for showing the effects in the case where the frequency of the ultrasonic wave is slightly shifted in relation to the condition shown in FIG. 4.

In the foregoing, there has been described the case of the condition where the wavelength of the ultrasonic wave propagated in the direction of the sheet thickness of the crystal grains each having the normal direction is set at a value of twice the thickness of the sheet multiplied by just integers or just half integers, so that the interferences of the multiple reflected waves with grains having normal orientation is increased, while the interference with grains having abnormal orientation is decreased. However, in the anisotropic silicon steel sheet, almost all of the grains are directed in the same orientation, and it was theoretically and experimentally ascertained that, when the orientation of the normal crystal grains was to be detected, it was preferable that the wavelength of the ultrasonic wave be set at a value slightly shifted from the value of twice the thickness of the sheet multiplied by the integers. More specifically, in FIG. 4, a frequency (10.33 MHz) of the ultrasonic wave is determined so that the wavelength of the ultrasonic wave propagated in the direction of [110] can be set at a value of the twice (0.6 mm) the sheet thickness (0.3 mm). In this case, as against the sonic speed (6200 m/s) of the crystal grains in the normal orientation, the intensity of the interferent multiple reflected waves becomes maximal and a dwelling point thereof is formed, whereby a change in the reflected intensity is low against a very small change in the sonic speed, so that an unsatisfactory sensitivity is shown. In contrast thereto, an example of the relationship between the sonic speed and the intensity of the reflected waves when the frequency of the ultrasonic wave is slightly shifted to 10.66 MHz (0.58 mm in terms of the wave length) is shown in FIG. 10. As is apparent from FIG. 10, against a change in the sonic speed of the grains in the normal orientation in the vicinity of 6200 m/s, a change in the intensity of the interferent multiple reflected waves is high, so that the measurement with high sensitivity of the grains in the normal orientation can be performed.

Figure 11:
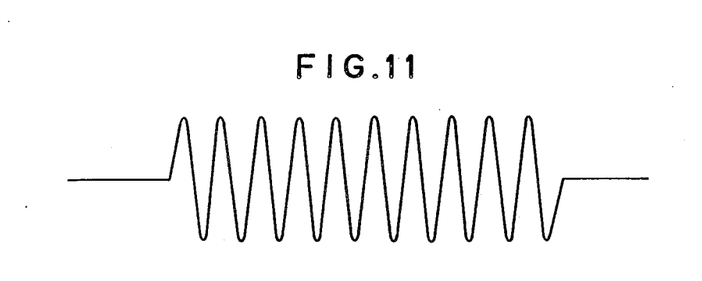
FIG. 11 is a chart showing an example of the wave form of the incident wave according to the present invention.

A second point to be noted in working the present invention is that, in order to cause the interference to easily occur, it is necessary to adopt two waves or more continuous pulse waves (burst waves) as the incident wave as shown in FIG. 11, instead of a single pulse. In terms of the interference, the more the number of burst waves is, the better the influence condition is. However, there are the problems of the longer duration of the surface reflected waves and the longer measuring time, so that the number of the burst waves can be set at about 10 to 20 waves actually.

According to the present invention, the distribution of the grains in the abnormal orientation of the metal sheet can be detected non-contactingly, non-distructively and rapidly. Accordingly, the disadvantages of the conventional macro-etch method can be obviated, that is, the working of peeling off the insulation coating film and the working of treating the chemicals for etching become unnecessary. Furthermore, the processing time of the inspection is shortened considerably. In the past, there has been no practical technique to be applied on-line, however, application of the present invention to on-line makes it possible to conduct the inspection over the total length relating to the abnormal grains of the product. Further, in an after-step of work such as a slitter step, portions of the abnormal grains are removed, whereby only portions of the normal grains are accepted as the product, so that excellent products can be delivered.

BRIEF DESCRIPTION OF THE DRAWINGS

The exact nature of this invention, as well as other objects and advantages thereof, will be readily apparent from consideration of the following specification relating to the accompanying drawings, in which like reference characters designate the same or similar parts throughout the figures thereof and wherein.

DESCRIPTION OF THE BEST MODE

One embodiment of the present invention will hereunder be described in detail with reference to the accompanying drawings.

Figure 1:
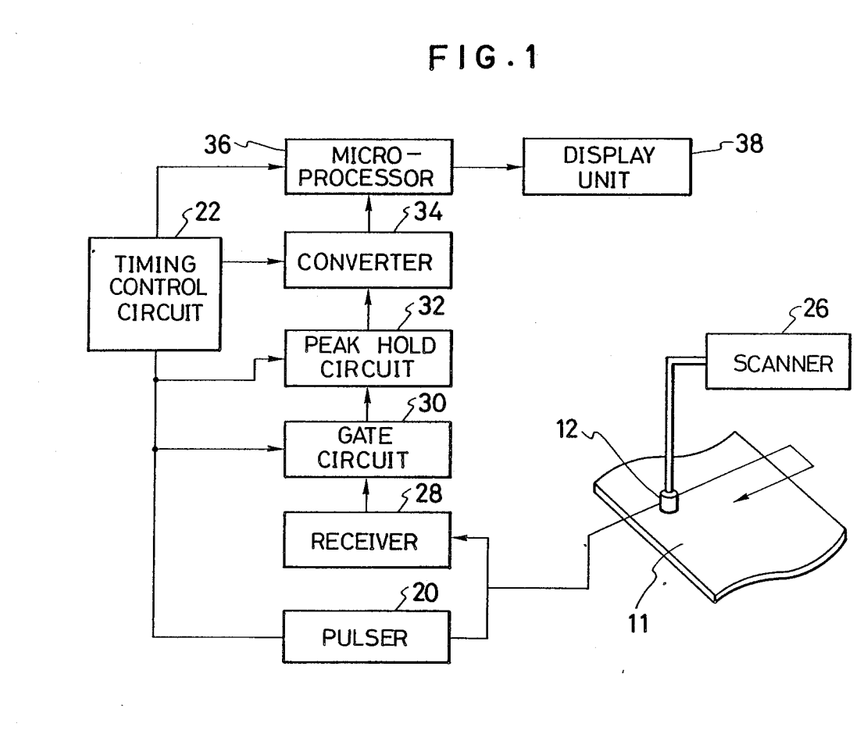
FIG. 1 is a block diagram, partially including an oblique view, showing the arrangement of one embodiment of the apparatus for measuring the distribution of the crystal grains in metal sheet according to the present invention.

The embodiment of the apparatus by the reflecting plate method according to the present invention is arranged as shown in FIG. 1.

A timing control circuit 22 outputs repetition pulses at a rate of 1–10 KHz for example, in association with a probe scanning speed of a scanner 26.

A pulser 20 produces an electric signal of about 10 burst waves having a frequency f given by an equation of $f = v/2d$, in synchronism with pulses from the timing control circuit 22.

An ultrasonic probe 12 which acts as a transmitting element and a receiving element as shown in FIG. 7 transduces the electric signal from the pulser 20 into an ultrasonic signal and output the same into a body 11 to be measured. The ultrasonic probe 12 is generally immersed in water together with the body 11, for example. Further, the scanner 26 causes the ultrasonic probe 12 to scan the surface of the body 11 in the two-dimensional directions.

A reflecting sheet 14 as shown in FIG. 7 is disposed beneath the body 11.

Ultrasonic reflected waves from the top and bottom faces of the body 11 are reflected by the reflecting plate 14 and are directed again into the ultrasonic probe 12 to be converted into electric signals therein.

A receiver 28, upon receiving the electric signals from the ultrasonic probe 12, suitably amplifies the electric signals and outputs the same into a gate circuit 30.

The gate circuit 30, in synchronism with a pulse from the timing control circuit 22, opens the gate circuit 30 with a predetermined delay, to thereby allow only the interferent multiple reflected signal R1 shown in FIG. 8 to be passed to a peak hold circuit 32.

The peak hold circuit 32, in synchronism with a pulse from the timing control circuit 22, detects a peak value of the signals from the gate circuit 30 during one repetition time until the following pulse comes, and holds the peak value for one repetition time.

Because a duration of the ultrasonic signal is on the order of only micro-second, a duration of the detected signals is lengthened in this peak hold circuit 32, so that analog-digital (A/D) conversion by an A/D converter 34 is facilitated.

The A/D converter 34 converts an analog signal from the peak hold circuit 32 into a digital signal in synchronism with a pulse from the timing control circuit 22 and outputs the same into a micro-processor 36.

The micro-processor 36 receives the digital signal from the A/D converter 34 and a probe position signal from the scanner 26, determines whether the grains are normal or abnormal from the magnitude of the interferent multiple reflected wave signal R1, and outputs the result into a display unit 38.

Incidentally, the apparatus for measuring the distribution of the crystal grains in orientation according to the present invention is assembled into a controller in a before-step or an after-step of work for example, whereby on-line control can be directly performed in accordance with the result of measuring. In this case, the display unit 38 may be dispensed with.

Action of the above embodiment will hereunder be described with reference to an example where a silicon steel sheet having a sheet thickness $d = 0.3$ mm is measured by this embodiment.

Figure 12:
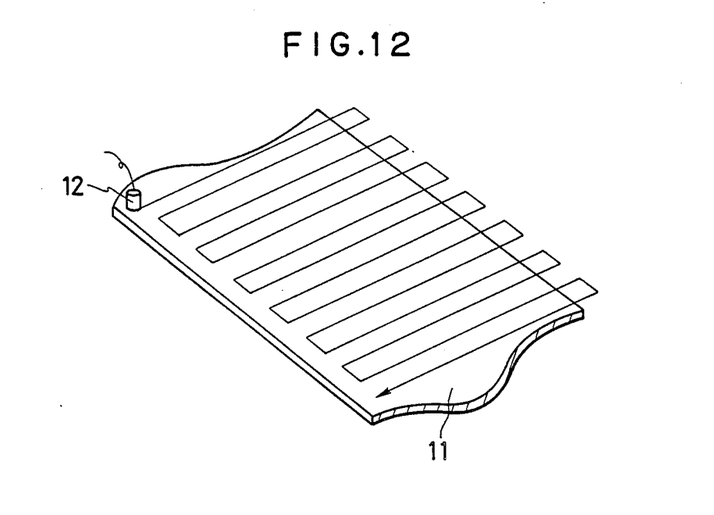
FIG. 12 is a perspective view showing an example of the scanning method of the ultrasonic probe in the embodiment shown in FIG. 1.

In this embodiment, the scanner 26 causes the ultrasonic probe 12 to scan the surface of the steel sheet 11 in the two-dimensional directions as shown in FIG. 12. Now, when a relative speed during scanning is set at 1 m/s, a scanning pitch at 0.5 mm and the repetition frequency of the pulse from the timing control circuit 22 at 2 KHz, the ultrasonic wave is directed into the steel sheet 11 at a rate of one per square of 0.5 mm by 0.5 mm.

The grain diameter of the crystal grain in the sheet plane of the anisotropic silicon steel sheet in the abnormal grain portion is 0.5–1 mm, and that in the normal grain portion is more than this. Therefore one or more ultrasonic pulses is directed into almost of all crystal grains, so that the magnitude of the interferent multiple reflected wave signal for all of the grains can be measured.

Furthermore, when the focus type ultrasonic probe capable of converging the ultrasonic wave is used as the ultrasonic probe 12 and the focal position is made substantially coincident with the center of the sheet thickness of the steel sheet 11, an ultrasonic wave beam having a diameter of about 0.5 mm can be easily obtained, and further, the distance between the steel sheet 11 and the probe 12 can be made as much as the focal length (several mm - several cm).

Next, while the scanning of this type is being performed, the intensities of the interferent multiple reflected waves R1, are successively detected by this embodiment.

When the frequency f of the ultrasonic wave is set at 10.33 MHz, the relationship between the intensity of reflection and the sonic speed in each of the crystal grain is the same as that shown in FIG. 4. Accordingly, when this intensity of reflection is displayed in synchronism with the scanning portion, this distribution pattern of the intensity represents the distribution of the crystal grains in orientation. Accordingly, determination can be made whether the product is good or bad in quality from the distribution of the measured values.

Figure 13:
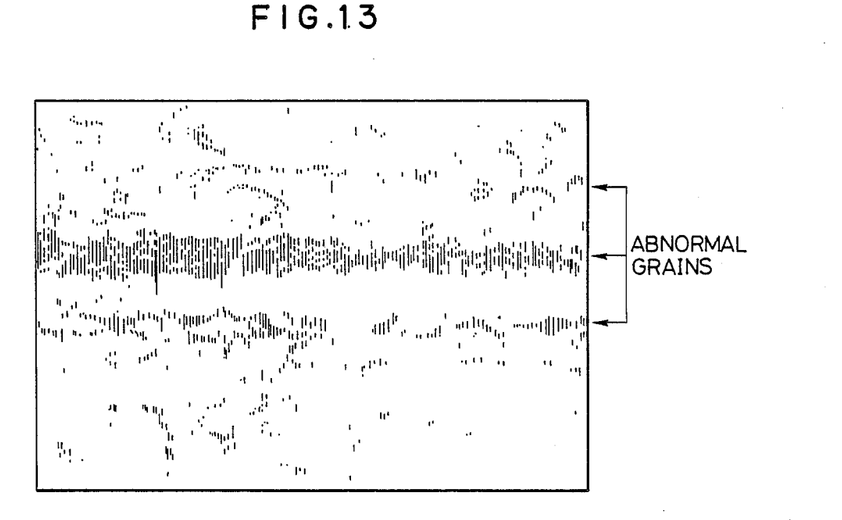
FIG. 13 is a chart showing an example of the result of measuring the distribution of the abnormal grains in the above embodiment.

FIG. 13 shows a case in which, when the number of burst waves of the ultrasonic wave is set at 10, only the portion of the abnormal grains are drawn black as an example of the result of measuring according to this embodiment. It can be ascertained that this result of measuring corresponds well to the result of measuring by the conventional macro-etch method. As described above, according to the present invention, the portion of the abnormal grains can be detected with high accuracy and non-destructively.

This embodiment is arranged such that a single ultrasonic probe 12 is combined with the reflecting plate 14 for use as shown in FIG. 7 (reflecting plate method), whereby, it is possible to measure from one side, a feature which is advantageous in on-line measurement in particular. Incidentally, the arrangement for transmitting and receiving the ultrasonic wave is not limited to this, and an arrangement such as that shown in FIG. 5 for example, may be used, in which an ultrasonic probe functioning as the transmitting element 12A and an ultrasonic probe functioning as the receiving element 12B are provided at positions opposed to each other, on opposite sides of the body 11 to be measured (transmission method). Furthermore, as shown in FIG. 2, an arrangement wherein the reflecting sheet 14 is dispensed with (simple reflection method) may be adopted.

Furthermore, in the above embodiment, one ultrasonic probe 12 has been used, however, when the body 11 to be measured is moved as in the on-line measurement and high speed measurement is required, a plurality (or a plurality of pairs) of ultrasonic probes may be used to increase the speed of measuring.

Incidentally, in the above embodiment, the frequency f of the ultrasonic wave has been determined such that the phase agree with each other when the speed is in the direction <110>. However, the frequency f may be determined such that the phases are shifted from each other by 180°, or, on the contrary, the frequency f may be determined in conformity with the speed of the abnormal orientation.

What is claimed is:

1. A method of measuring a distribution of crystal grains in metal sheet, comprising:
   determining an exciting frequency of ultrasonic wave such that a wavelength of ultrasonic wave propoagated in a direction of the sheet thickness of the grains each having an aimed orientation is set at a value of twice the thickness of the sheet multiplied by about integers or about half integers;
   directing into the sheet thickness burst-like ultrasonic pulses having said frequency and including two or more waves by use of at least one ultrasonic probe moving relatively with the metal sheet;
   causing multiple reflected waves generated from the bottom and top faces of the metal sheet upon the reflection from the sheet surface to interfere with each other;
   detecting said multiple reflected waves, which have interfered with each other;
   estimating orientations of the grains in the metal sheet from the magnitudes in amplitude of said interferent multiple reflected waves; and
   two-dimensionally detecting the distribution of the grains in orientation in various portions, into which the ultrasonic wave is directed.

2. The method as set forth in claim 1, wherein the presence of abnormal grains, each having random crystal orientation, is detected when the intensity of the interferent multiple reflected waves is lower than a predetermined value.

3. The method as set forth in claim 1, wherein said exciting frequency of the ultrasonic wave is determined such that the wavelength of the ultrasonic wave is set at a value slightly shifted from the value of twice the thickness of the sheet multiplied by integers or half integers.

4. The method as set forth in claim 1, wherein the number of waves of said burst-like ultrasonic pulses is set at 10–20.

5. An apparatus for measuring a distribution of crystal grains in metal sheet, comprising:
   ultrasonic probes, one acting as a transmitting element and the other as a receiving element, which are respectively provided at positions opposed to each other and on opposite sides of a body to be measured, for interchanging an electric signal and ultrasonic wave;
   a transmitting means for delivering to the transmitting element two or more continuous burst wave electric signals having a frequency determined such that a wavelength of the ultrasonic wave propagated in a direction of the sheet thickness of the crystal grains each having an aimed orientation is set at a value of twice the thickness of the sheet multiplied by about integers or about half integers;
   a receiving means for receiving a signal generated at the receiving element;
   a means for taking out a signal produced by the interference between multiple reflected waves from the bottom and top face of the metal sheet, which are generated upon the reflection from the sheet surface, from signals received by the receiving means; and
   a means for determining whether the orientation of the grains, at portions into which the ultrasonic wave is directed, is normal or not, from the magnitudes in amplitude of the interferent multiple reflected waves.

6. The apparatus as set forth in claim 5, wherein a focus type ultrasonic probe capable of converging the ultrasonic wave is used as said ultrasonic probe, and the focal position thereof is made substantially coincident with the center of the sheet thickness of the metal sheet.

7. An apparatus for measuring a distribution of crystal grains in metal sheet, comprising:
- an ultrasonic probe acting as a transmitting and as a receiving element, which is provided on one side of the metal sheet, for interchanging an electric signal and ultrasonic wave;
- a reflecting plate provided on the other side of said ultrasonic probe such that the metal sheet is positioned between said reflecting plate and said ultrasonic probe;
- a transmitting means for transmitting two or more continuous burst wave electric signals having a frequency determined such that a wavelength of the ultrasonic wave propagated in a direction of the sheet thickness of the crystal grains each having an aimed orientation is set at a value of twice the thickness of the sheet multiplied by about integers or about half integers, to said ultrasonic probe;
- a receiving means for receiving a signal generated at said ultrasonic probe after being reflected by the reflecting plate and penetrating through the body again;
- a means for taking out a signal produced by the interference between multiple reflected waves from the bottom and top faces of the metal sheet, which are generated upon the reflection from the sheet surface, from signals received by said receiving means; and
- a means for determining whether the orientation of the grains at portions, into which the ultrasonic wave is directed, is normal or not, from the magnitudes in amplitude of the interferent multiple reflected waves.

8. The apparatus as set forth in claim 7, wherein an ultrasonic wave reflecting portion of said reflecting plate is concave, and the ultrasonic wave reflected by the concave surface is focused at about the center of the plate thickness of the metal sheet.

9. An apparatus for measuring a distribution of crystal grains in metal sheet, comprising:
- at least one ultrasonic probe for interchanging an electric signal and ultrasonic wave;
- a scanner for scanning said ultrasonic probe or probes in the two-dimensional directions;
- a pulser for transmitting two or more continuous burst wave electric signals having a frequency determined such that a wavelength of the ultrasonic wave propagated in a direction of the sheet thickness of the crystal grains each having an aimed orientation is set at a value of twice the thickness of the sheet multiplied by about integers or about half integers;
- a receiver for receiving a signal from said ultrasonic probe;
- a timing control circuit for controlling the driving of the pulser;
- a gate circuit for taking out only a signal produced by the interference between multiple reflected waves from the bottom and top faces of the metal sheet, excluding signals generated by the reflected waves from the sheet surface, in synchronism with a pulse emitted from the timing control circuit;
- a peak hold circuit for holding a peak value of the interferent signal for a predetermined period of time;
- an analog/digital converter for analog/digital converting an output from the peak hold circuit;
- a processing unit for receiving an output from the analog/digital converter and performing a predetermined operation to determine whether the orientation of the crystal grains at portions, into which the ultrasonic wave is directed, is normal or not, and calculating the distribution of the grains having abnormal orientations on the basis of positional information from the scanner; and
- a display unit for displaying the calculated results.

10. The apparatus as set forth in claim 9, wherein a propagation course of the ultrasonic wave as a whole is immersed in water.

* * * * *